(12) United States Patent
Alexander

(10) Patent No.: US 10,986,913 B1
(45) Date of Patent: Apr. 27, 2021

(54) STETHOSCOPE HOLDER

(71) Applicant: Kolton Alexander, Hays, KS (US)

(72) Inventor: Kolton Alexander, Hays, KS (US)

( * ) Notice: Subject to any disclaimer, the term of this patent is extended or adjusted under 35 U.S.C. 154(b) by 0 days.

(21) Appl. No.: 16/667,329

(22) Filed: Oct. 29, 2019

(51) Int. Cl.
*A45F 5/02* (2006.01)
*A61B 7/02* (2006.01)

(52) U.S. Cl.
CPC . *A45F 5/02* (2013.01); *A61B 7/02* (2013.01)

(58) Field of Classification Search
CPC .... A45F 5/02; A45F 5/021; A45F 2200/0566; A45F 2200/05; A61B 7/02; A61B 90/50; A61B 90/53
USPC ................ 224/250, 915, 677, 667; 248/693; 294/149–150, 157
See application file for complete search history.

(56) References Cited

U.S. PATENT DOCUMENTS

| | | | | | |
|---|---|---|---|---|---|
| 755,009 | A | * | 3/1904 | Igel | A45F 5/02 224/250 |
| 3,300,109 | A | * | 1/1967 | Clark | F41C 33/048 224/667 |
| 4,667,374 | A | * | 5/1987 | Bianchi | A41F 9/002 224/667 |
| D300,989 | S | * | 5/1989 | Kovach | 224/916 |
| 4,912,779 | A | * | 4/1990 | Laird | A61F 9/045 2/12 |
| 5,451,725 | A | * | 9/1995 | Goldman | A45F 5/02 181/131 |
| 5,505,356 | A | * | 4/1996 | Noriega | A45F 3/14 224/250 |
| 5,660,309 | A | * | 8/1997 | Belanger | A45B 11/02 224/250 |
| D425,353 | S | * | 5/2000 | Foy | D24/134 |
| 6,065,563 | A | * | 5/2000 | Stowers | A45F 5/02 181/131 |
| 6,152,338 | A | * | 11/2000 | Smith | A01K 97/10 224/149 |
| 6,264,079 | B1 | * | 7/2001 | Skaggs | F41C 33/0236 224/193 |
| 6,484,918 | B1 | * | 11/2002 | Lefebvre | A45F 5/02 181/131 |
| 7,641,085 | B2 | * | 1/2010 | Nickels | A45F 3/08 224/190 |
| 2008/0116239 | A1 | * | 5/2008 | Lu | A45F 3/14 224/575 |
| 2010/0018104 | A1 | * | 1/2010 | Pedersen | A01K 97/10 43/21.2 |
| 2014/0374452 | A1 | * | 12/2014 | Hammers | F41C 33/048 224/243 |

* cited by examiner

*Primary Examiner* — Adam J Waggenspack
(74) *Attorney, Agent, or Firm* — Intellectual Property Center, LLC; Arthur K. Shaffer

(57) ABSTRACT

The present invention provides an improved stethoscope holder for receiving a stethoscope during movement from various medical locations which includes a holder, an elongated strap secured to the holder and operable between an open and a closed position, a conical pocket, a fastening mechanism including a pair of fasteners, the fastening mechanism releasably securing the elongated strap in the closed position, the pair of fasteners aligned along an axis of symmetry and a clip.

8 Claims, 5 Drawing Sheets

US 10,986,913 B1

STETHOSCOPE HOLDER

FIELD OF THE INVENTION

The present invention is broadly directed to pocket holders and more particularly to a easily accessible, quick acting stethoscope holder adapted for use by a medical professional for retaining a stethoscope within an article of clothing while preforming medical tasks.

BACKGROUND OF THE INVENTION

Stethoscopes are an essential tool to listing and evaluating a patient's health. They have been used for decades to examine and evaluate a patient's health. Medical professionals such as doctors, nurses, nurse practitioners and other medical personnel often need to carry a stethoscope as part of checking on patients' health. Typically, stethoscopes have a number of long, flexible tubes designed to extend a substantial distance between a bell which can be placed around the patient's body and a pair of ear temples. Because these tubes are long and flexible, they easily become tangled and are difficult to manage and maintain.

To avoid tangling the tubes, some medical personnel wear the stethoscope continually around or near their neck as they travel between patients in and around a medical facility. However, the stethoscope can easily fall off their neck and become damaged. In addition, wearing them around a neck for long periods of time can be difficult or unconformable. In some cases, medial personnel place or store the stethoscope loosely in a pocket of a shirt or lab coat along with other objects such as keys, pens or pads of paper to use while examining and evaluating their patients. However, this does not prevent the tubes from becoming tangled or from becoming dirty. In addition, when repeatedly pulling the stethoscope out from a pocket, the stethoscope may become damaged or the pocket may become damaged and the stethoscope may need to become untangled.

Some stethoscope holders are rigid and fixed and can only be used which various rigid structural elements which have predefined arrangements for using a stethoscope. However, some of these rigid and inflexible stethoscope holders lack the flexibility and adaptability for use with varying dimensioned stethoscopes to hold them in varying orientations. In addition, these rigid and inflexible stethoscope holders are not easy to use or quick to release the stored stethoscope.

Currently, there is no convenient way to carry and store a stethoscope which allows for quick and easy release for use while also allowing for convenient storage during non-use.

Accordingly, there is a need for a convenient way to carry and store a stethoscope which allows for quick and easy release while carrying for the stethoscope and which addresses at least a portion of the aforementioned shortcomings.

SUMMARY OF THE INVENTION

The present invention includes an improved stethoscope holder for receiving a stethoscope, the stethoscope holder comprising a pocket holder, an elongated strap secured to said pocket holder and operable between an open position and a closed position, a conical pocket presented by said elongated strap in said closed position, a fastening mechanism including a pair of fasteners, one of said pair of fasteners associated with said pocket holder, a second one of said pair of fasteners being associated with said elongated strap, said fastening mechanism releasably securing said elongated strap in said closed position, said one of said pair of fasteners rotationally aligned with said second one of said pair of fasteners along an axis of symmetry, a clip secured to said pocket holder for securing said improved stethoscope holder during use.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

DETAILED DESCRIPTION OF THE INVENTION

Figure 1:
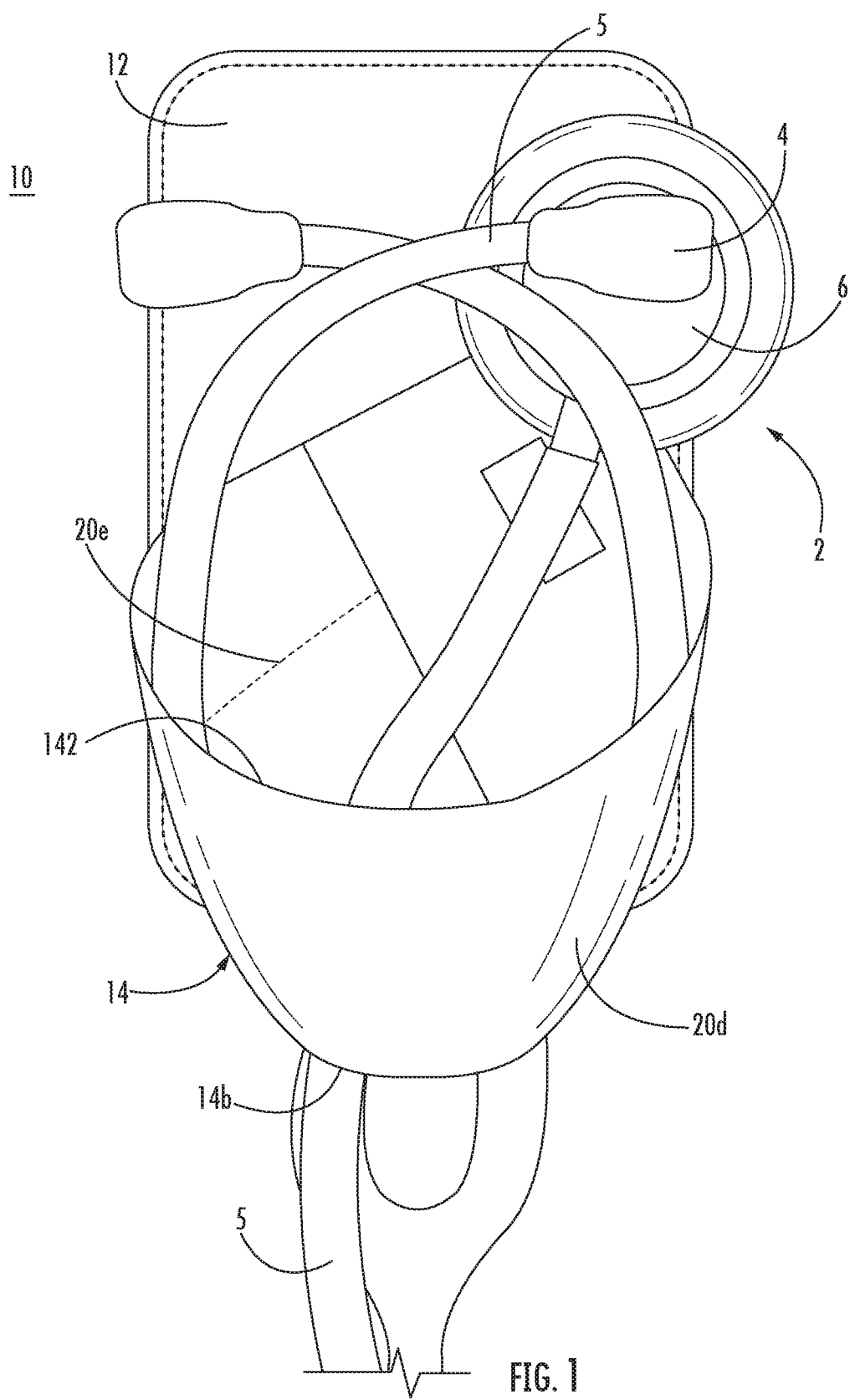
FIG. 1 is a front perspective view of an exemplary embodiment of the improved stethoscope holder in receipt of an exemplary stethoscope.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 10 generally refers to an embodiment of the present invention, an improved stethoscope holder adapted for receipt of a typical stethoscope 2 with a conical pocket 14.

As is generally known, a typical stethoscope 2 includes rubber tubing 5 which extends between a chest piece, also called a bell 6, to a pair of ear pieces 4. Typically, during use, the improved stethoscope holder 10 is maintained in the stored configuration with the strap 20 coiled into the closed orientation presenting the conical pocket 14 for receipt of the stethoscope 2.

Figure 2:
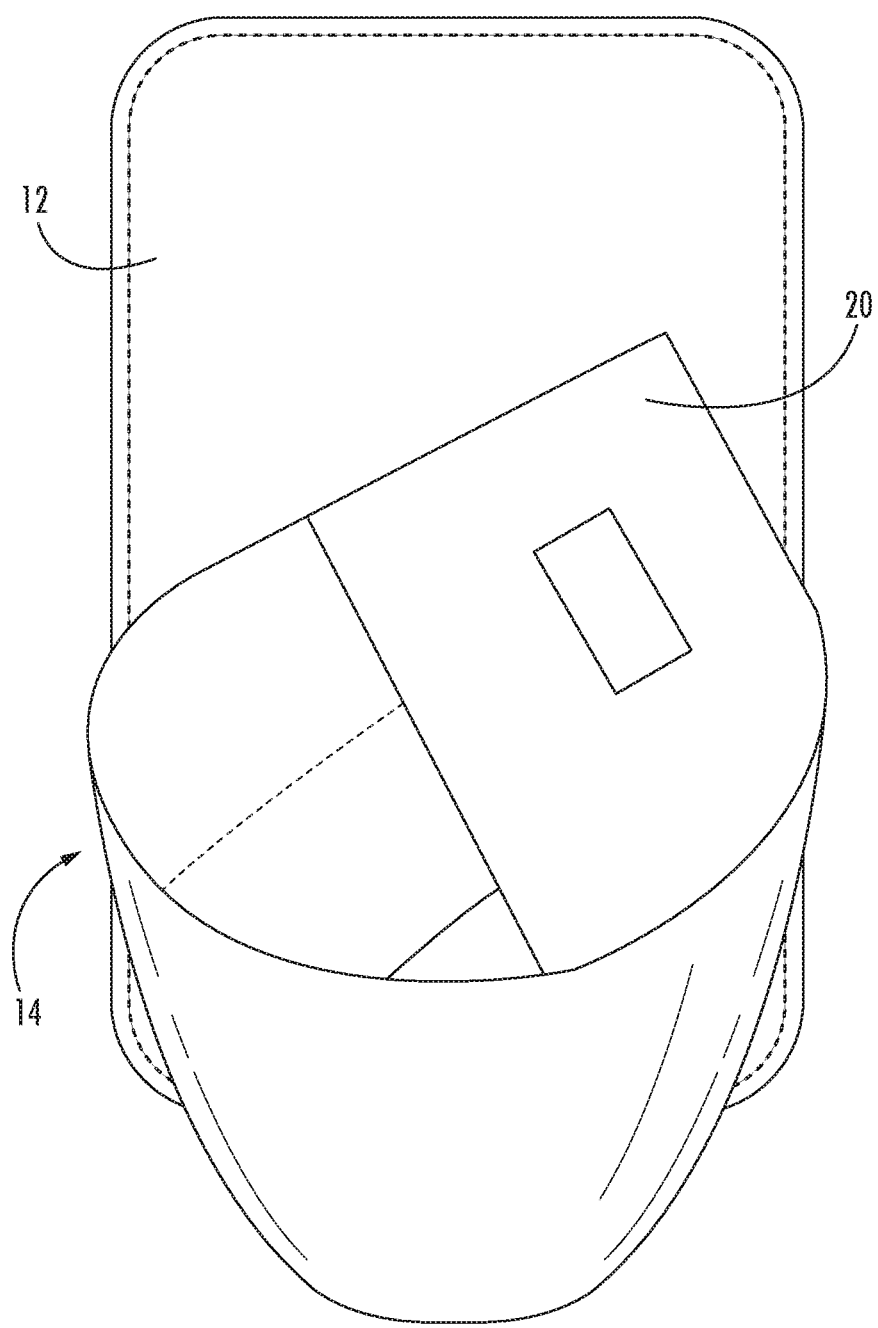
FIG. 2 is a front elevation of the exemplary embodiment of the improved stethoscope holder of FIG. 1 in the closed position.

As illustrated in FIGS. 1-2, the depicted embodiment of the improved stethoscope holder 10 includes a pocket holder 12 with a frontside 12a opposite a backside 12b. The frontside 12a generally presents the conical pocket 14. Generally, the conical pocket 14 extends upward from a bottom 14a to a top 14b, the bottom 14a having a smaller diameter opening and the top 14b having a larger diameter opening, the top 14b and bottom 14a being generally open therethrough for receipt of the stethoscope 2. In one embodiment, the conical pocket 14 is formed by rotating the distal end 20b of the elongated strap 20 circularly so that an outer surface 20d of the elongated strap 20 of the elongated strap 20 is turned inwardly for joining the distal end 20b to the proximate end 20a. In operation, the distal end 20b is released quickly and easily from the pocket holder 12. The conical pocket 14 includes a generally conical shape for receipt of the stethoscope and for being easily fastened and unfastened by securing and releasing the distal end 20b of the strap 20 and allowing it to extend downward, for rapid release of the stethoscope 2.

The elongated strap 20 is generally rectangularly shaped and elongated as it extends from the proximate end 20a to the distal end 20b. Straps being generally known may utilize a variety of shapes and dimensions. As depicted, the elongated strap 20 includes an aperture 20c through the proximate end 20a for extension of the fastener 24 therethrough to the pocket holder 12. The elongated strap 20 is generally constructed from a lightweight, flexible, woven material which can support the weight of a typical stethoscope 2 and which can be used repeatedly for carrying the stethoscope 2 around various locations.

The pocket holder 12 is generally constructed from a rigid, weather resistant, resilient material which can support a clip 30 and the conical pocket 14 along with securing the proximate end 20a while allowing for the repeated release of the distal end 20b. The pocket holder 12 may be fabricated from manmade or synthetic materials and while being depicted as generally rectangular, may have varying shapes and sizes as desired.

Figure 3:
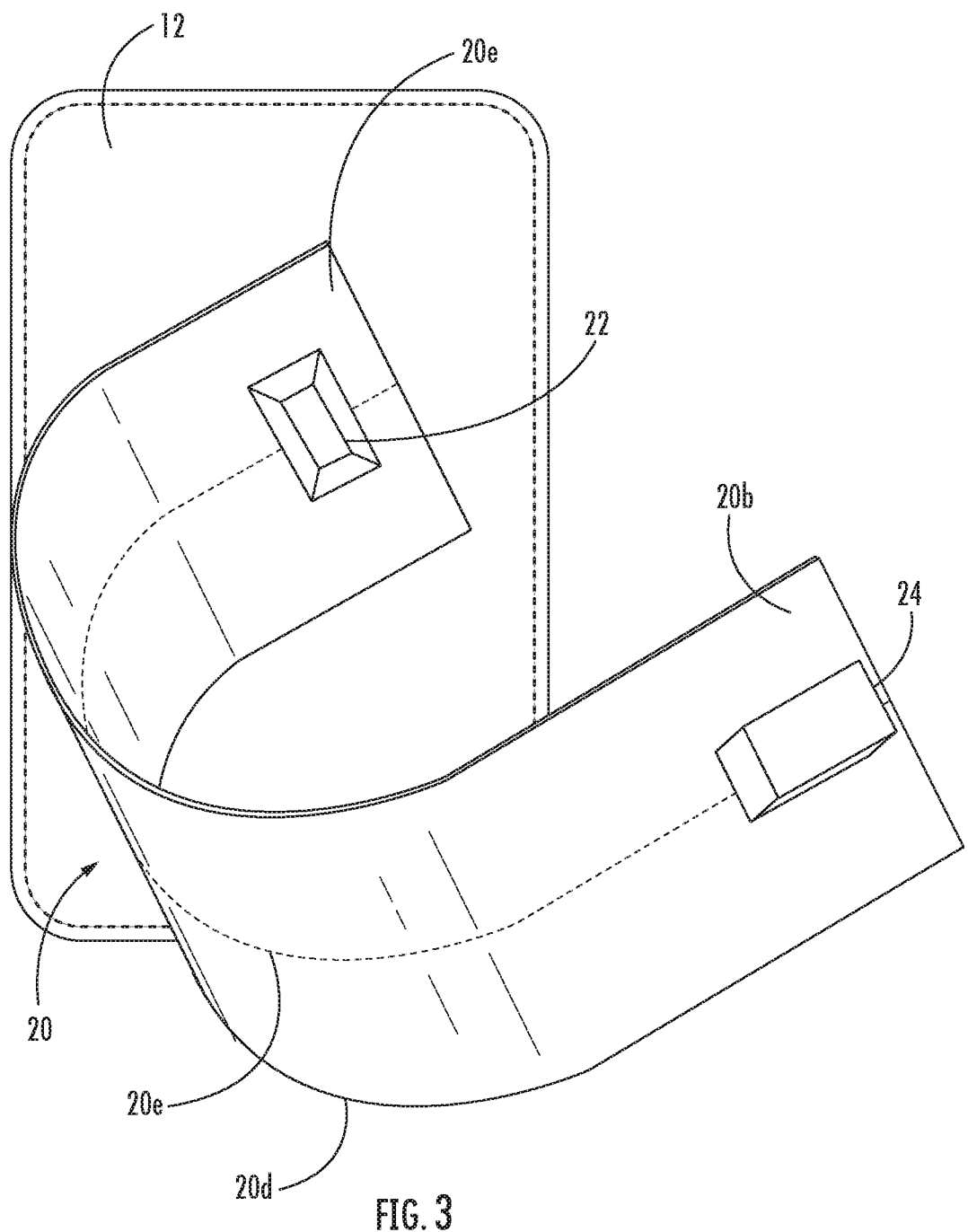
FIG. 3 is a front elevation of the exemplary embodiment of the improved stethoscope holder of FIG. 1 in the released position.

In use, the improved stethoscope holder 10 extends from an unfastened position illustrated in FIG. 3 and a fastened position illustrated in FIGS. 1-2. As further illustrated in the unfastened embodiment illustrated in FIG. 3, the frontside 12a includes a receiver 22 which is secured to a proximate end 20a of the elongated strap 20 with a fastening mechanism. The depicted embodiment of the fastening mechanism includes the rectangular receiver 22 configured for releasable receipt of the rectangular fastener 24, although other complementary shaped fasteners may be utilized. The depicted fastening mechanism illustrated in FIGS. 3, 5-6 utilizes a mechanical, like a key or keyed assembly or a magnetic fastening mechanism but other fastening mechanism may be utilized within the scope of the present invention. In the depicted embodiment the rectangular fastener 24, is spaced along the elongated strap 20 for receipt by the rectangular receiver 22 which is located on the pocket holder 12 for receipt of the rectangular fastener 24 through the proximate end 20a. Use of magnetic materials or structures of opposite polarity may allow for more secure and easier repeatable release of the rectangular fastener 24 from the rectangular receiver 22. Alternatively, the elongated strap 20 may incorporate oppositely charged sections within the distal 20b and proximate ends 20a. Alternatively, other fastener types may be utilized including hook and loop type fasteners which allow for rapid, repeated release and easy and secure replacement of the elongated strap 20, presenting the conical pocket 14 for receipt of the stethoscope 2.

As further illustrated in FIG. 3, an axis of symmetry 20e extends along said elongated strap 20 from the proximate end 20a to the distal end 20b. In general, the fastening mechanism includes a pair of fasteners, a first fastening member associated with the proximate end 20a and a second fastening member associated with the distal end 20b. In one embodiment, the first fastening member and the second fastening member are aligned along the axis of symmetry 20e. In the depicted embodiment of FIG. 3, the first fastening member and second fastening member are rotationally aligned along the axis of symmetry 20e, the rotational alignment corresponding to the rotation of the elongated strap 20 in forming the conical pocket 14. In this way, the fastening mechanism is aligned after rotation of the elongated strap 20 from the open position to a closed position associated with forming the conical pocket 14 which receives the stethoscope 2.

An embodiment of the first fastening mechanism is illustrated in FIG. 3 as the receiver 22 and includes a pair of backward extending sidewalls from the frontside 12a towards the backside 12b. The receiver 22 has generally complementary structure for receiving the embodiment of the second fastening mechanism illustrated in FIG. 3 as the releasable fastener 24. As illustrated, the receiver 22 is generally associated with the proximate end 20a and the releasable fastener 24 is associated with the distal end 20. The conical pocket 14 generally provides sufficient structure for receiving a typical stethoscope 2 while the pocket holder 12 generally has sufficient structure for securing the conical pocket 14 for storing the stethoscope 2 during movement between various medical destinations and for quick release of the stethoscope 2 as desired.

Figure 4:
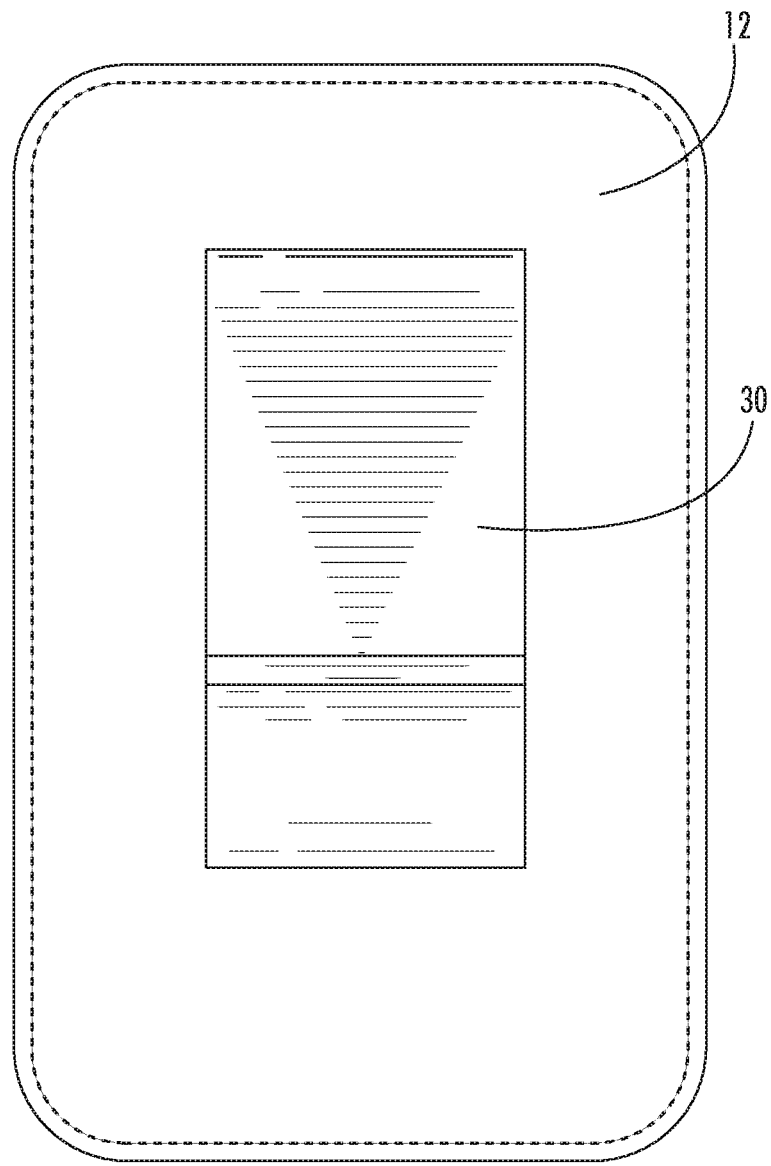
FIG. 4 is a rear elevation of the exemplary embodiment of the improved stethoscope holder illustrated in FIG. 1 illustrating an exemplary clip.
Figure 5:
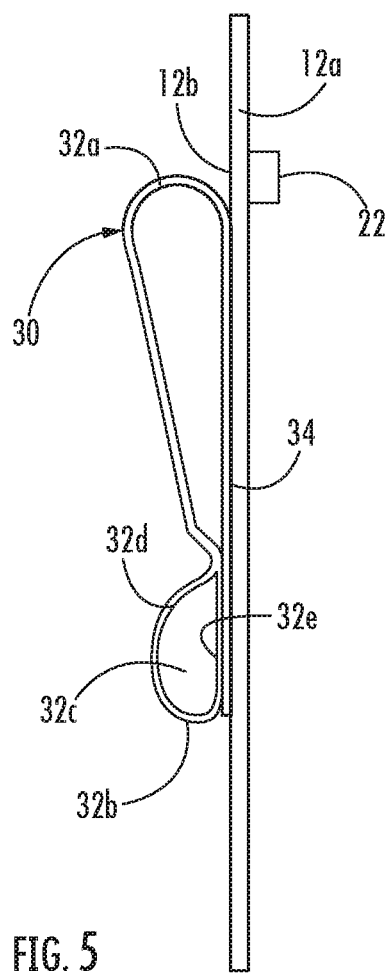
FIG. 5 is an elevation of an exemplary closure mechanism associated with the improved stethoscope holder illustrated in FIG. 1.
Figure 6:
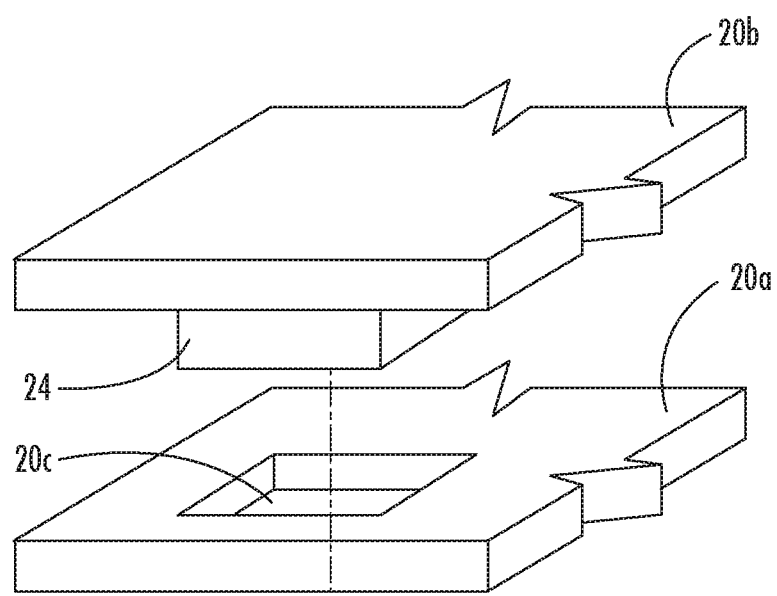
FIG. 6 is an alternative elevation of an exemplary closure mechanism associated with the improved stethoscope holder of FIG. 1.

As further illustrated in FIGS. 4-5, the backside 12b generally presents the clip 30 for securing the improved stethoscope holder 10 to an article of clothing (not shown) like a shirt or pant's pocket or along a belt or lapel. The clip 30 extends rearward from the base 12 and may be a typical clothing fastener or as depicted in FIG. 5 may include two regions, an upper region 32a and a lower region 32b, the upper region 32a being generally elliptical for receiving a portion of clothing (not shown), for example, and the lower region 32b presenting a boss 32c with a curved outer surface 32d opposite a flat underside 32e, the boss 32c biased towards an underlying support 34. The boss 32c and the underlying support 34 present an ergonomically contoured fastener for securing the base 12 to an article of clothing or an accessory like a belt (not shown), for example, during use and allowing for selective separation of the boss 32c from the underlying support 34 as desired for selectively removing the improved stethoscope holder 10 from the clothing or other accessory. The clip 30 is generally mounted to the backside 12b near the middle of the pocket holder 12. The first fastener 22 is illustrated extending towards the front of the base 12 along the frontside 12a for securing the second fastener 24 during use of the stethoscope holder 10.

In general, the clip 30 includes a fixed, biasing or hinged structure operable for anchoring the pocket holder 12. Generally, the clip 30 is biased or hinged towards a closed position for repeatable pivoted operation of the clip 30. In this way, the biasing structure directs the clip 30 towards a closed position for anchoring the improved stethoscope holder 10 to an article of clothing, a purse, a belt or the like (not shown).

It is to be understood that while certain forms of the present invention have been illustrated and described herein, it is not to be limited to the specific forms or arrangement of parts described and shown.

What is claimed and desired to be secured by Letters Patent:

1. An improved stethoscope holder for receiving a stethoscope, the stethoscope holder comprising:
    a pocket holder;
    a rectangular strap having a proximate and distal end, said
        proximate end releasably secured to said pocket holder
        and spaced from said distal end along an axis of
        symmetry;

said distal end having a fastener positioned along the axis of symmetry on an outer surface;

a receiver configured for receiving said fastener therethrough and presented by said proximate end of said rectangular strap, said receiver being in rotational alignment with said fastener; and a conical pocket formed by inward rotation of said distal end wherein said outer surface is rotated about said axis of symmetry for extending said fastener through said receiver to said pocket holder, said inward rotational corresponding to said rotational alignment between said receiver and said fastener.

2. The improved stethoscope holder of claim 1 wherein said rectangular strap is flexible.

3. The improved stethoscope holder of claim 1 wherein said pocket holder further comprises a frontside which presents said conical pocket.

4. The improved stethoscope holder of claim 1 wherein said conical pocket extends downwardly for receipt of a stethoscope.

5. The improved stethoscope holder of claim 1 wherein said fastener and said receiver are rectangular.

6. The improved stethoscope holder of claim 1 wherein said fastener is a repeatable quick release fastener.

7. The improved stethoscope holder of claim 1, said pocket holder further comprising a rearwardly extending anchor having an upper region spaced from a lower region.

8. An improved stethoscope holder comprising:

a pocket holder;

a rectangular strap having a proximate end spaced opposite a distal end, said proximate end and said distal end being symmetrically aligned;

said rectangular strap secured at said proximate end to said pocket holder;

a fastener associated with said distal end;

a receiver associated with said proximate end and configured for rotated receipt of said fastener;

said rectangular strap operable between a closed position and an open position by rotating said distal end; and wherein when in said closed position the rectangular strap forms a conical pocket, said conical pocket formed by coiling said distal end for rotated passage of said fastener through said receiver to said pocket holder.

\* \* \* \* \*